US011231420B2

(12) United States Patent
Banerjee et al.

(10) Patent No.: US 11,231,420 B2
(45) Date of Patent: Jan. 25, 2022

(54) SELECTION AND OPTIMIZATION OF APTAMERS TO RECOGNIZE EBOLA MARKERS

(71) Applicant: Aptalogic Inc., Ames, IA (US)

(72) Inventors: Soma Banerjee, Ames, IA (US); Marit Nilsen-Hamilton, Ames, IA (US)

(73) Assignee: APTALOGIC, INC., Ames, IA (US)

( * ) Notice: Subject to any disclaimer, the term of this patent is extended or adjusted under 35 U.S.C. 154(b) by 102 days.

(21) Appl. No.: 16/378,073

(22) Filed: Apr. 8, 2019

(65) Prior Publication Data
US 2019/0310252 A1 Oct. 10, 2019

Related U.S. Application Data

(60) Provisional application No. 62/654,778, filed on Apr. 9, 2018.

(51) Int. Cl.
*G01N 33/569* (2006.01)
*C12N 15/113* (2010.01)

(52) U.S. Cl.
CPC ... *G01N 33/56983* (2013.01); *C12N 15/1131* (2013.01); *C12N 2310/16* (2013.01); *C12N 2310/323* (2013.01)

(58) Field of Classification Search
None
See application file for complete search history.

(56) References Cited

U.S. PATENT DOCUMENTS

| | | | |
|---|---|---|---|
| 7,855,054 B2 | 12/2010 | Schneider et al. | |
| 8,409,795 B2 | 4/2013 | Schneider et al. | |
| 9,134,247 B2 * | 9/2015 | Sengupta | G01N 33/54373 |
| 9,651,556 B2 | 5/2017 | Bock et al. | |

OTHER PUBLICATIONS

Banerjee, J. & Nilsen-Hamilton, M. "Aptamers: multifunctional molecules for biomedical research". J Mol Med (Berl) 91, 1333-1342 (2013) [http://www.ncbi.nlm.nih.gov/pubmed/24045702].

Bassett, S.E., et al. "Combinatorial Selection and Edited Combinatorial Selection of Phosphorothioate Aptamers Targeting Human Nuclear Factor-κB RelA/p50 and RelA/RelA". Biochemistry 43, 9105-9115 (2004) [http://dx.doi.org/10.1021/bi036220h].

Gold, L., et al. "Aptamer-Based Multiplexed Proteomic Technology for Biomarker Discovery". PLoS One 5, e15004 (2010) [http://www.ncbi.nlm.nih.gov/pubmed/21165148].

Hong, S., et al. "Ebola Virus Aptamers: From Highly Efficient Selection to Application on Magnetism-Controlled Chips" (2019) Analytical Chemistry. 91. 10.1021/acs.analchem.8b04623.

Miller, J. "Diagnosing Ebola in minutes". Harvard Gazette 2015 (2015).

Sachan, A. "Specificity and Ligand Affinities of the Cocaine Aptamer: Impact of Structural Features and Physiological NaCl." Anal Chem 88, 7715-7723 (2016) [http://www.ncbi.nlm.nih.gov/pubmed/27348073].

Sanchez, A., et al. "Detection and Molecular Characterization of Ebola Viruses Causing Disease in Human and Nonhuman Primates". The Journal of infectious diseases 179 Suppl 1, S164-169 (1999) [http://www.ncbi.nlm.nih.gov/pubmed/9988180].

Sanchez, A., et al. "Biochemical Analysis of the Secreted and Virion Glycoproteins of Ebola Virus". Journal of Virology 72, 6442-6447 (1998) [http://www.ncbi.nlm.nih.gov/pubmed/9658086].

Schneider, D. et al. "Selection of High Affinity RNA Ligands to the Bacteriophage R17 Coat Protein" J. Mol. Biol. (1992) 228, 862-869.

Shubham, S., et al. "A 2'FY-RNA Motif Defines an Aptamer for Ebolavirus Secreted Protein" Sci Rep 8, 12373 (2018) doi:10.1038/s41598-018-30590-8.

Urbanowicz, R.A., et al. "Human Adaptation of Ebola Virus during the West African Outbreak". Cell 167, 1079-1087. e1075 (2016) [http://dx.doi.org/10.1016/j.cell.2016.10.013].

Vivekananda, J., et al. "Anti-Francisella tularensis DNA aptamers detect tularemia antigen from different subspecies by Aptamer-Linked Immobilized Sorbent Assay" Lab Invest. Jun. 2006; 86(6):610-618.

* cited by examiner

*Primary Examiner* — Shanon A. Foley
*Assistant Examiner* — Myron G Hill
(74) *Attorney, Agent, or Firm* — Westman, Champlin & Koehler, P.A.; Visala C. Goswitz

(57) ABSTRACT

Aptamers have been identified that bind to the sGP protein in ebola virus. The aptamers are single stranded DNA aptamers. The aptamers have high specificity and bind sGP in serum samples. The aptamers can be used to detect infection of individuals with ebola virus. Methods for detecting ebola virus in an individual are disclosed.

16 Claims, 3 Drawing Sheets

Specification includes a Sequence Listing.

Fig. 2

SEQUENCE LISTING

```
<160> NUMBER OF SEQ ID NOS: 17

<210> SEQ ID NO 1
<211> LENGTH: 100
<212> TYPE: DNA
<213> ORGANISM: Artificial Sequence
<220> FEATURE:
<223> OTHER INFORMATION: DNA single stranded oligonucleotide library
<220> FEATURE:
<221> NAME/KEY: misc_feature
<222> LOCATION: (25)..(77)
<223> OTHER INFORMATION: n is a, c, g, or t

<400> SEQUENCE: 1
gcctgttgtg agcctcctgt cgaannnnnn nnnnnnnnnn nnnnnnnnnn nnnnnnnnnn       60
nnnnnnnnnn nnnnnnnttg agcgtttatt cttgtctccc                           100

<210> SEQ ID NO 2
<211> LENGTH: 21
<212> TYPE: DNA
<213> ORGANISM: Artificial Sequence
<220> FEATURE:
<223> OTHER INFORMATION: A synthetic primer

<400> SEQUENCE: 2
gggagacaag aataaacgct c                                                21

<210> SEQ ID NO 3
<211> LENGTH: 24
<212> TYPE: DNA
<213> ORGANISM: Artificial Sequence
<220> FEATURE:
<223> OTHER INFORMATION: A synthetic primer

<400> SEQUENCE: 3
gcctgttgtg agcctcctgt cgaa                                             24

<210> SEQ ID NO 4
<211> LENGTH: 52
<212> TYPE: DNA
<213> ORGANISM: Artificial Sequence
<220> FEATURE:
```

<223> OTHER INFORMATION: A synthetic primer

<400> SEQUENCE: 4
tccctacacg acgctcttcc gatctatcac ggggagacaa gaataaacgc tc            52

<210> SEQ ID NO 5
<211> LENGTH: 52
<212> TYPE: DNA
<213> ORGANISM: Artificial Sequence
<220> FEATURE:
<223> OTHER INFORMATION: A synthetic primer

<400> SEQUENCE: 5
tccctacacg acgctcttcc gatcttagct tgggagacaa gaataaacgc tc            52

<210> SEQ ID NO 6
<211> LENGTH: 52
<212> TYPE: DNA
<213> ORGANISM: Artificial Sequence
<220> FEATURE:
<223> OTHER INFORMATION: A synthetic primer

<400> SEQUENCE: 6
tccctacacg acgctcttcc gatctggcta cgggagacaa gaataaacgc tc            52

<210> SEQ ID NO 7
<211> LENGTH: 52
<212> TYPE: DNA
<213> ORGANISM: Artificial Sequence
<220> FEATURE:
<223> OTHER INFORMATION: A synthetic primer

<400> SEQUENCE: 7
tccctacacg acgctcttcc gatctagtca agggagacaa gaataaacgc tc            52

<210> SEQ ID NO 8
<211> LENGTH: 52
<212> TYPE: DNA
<213> ORGANISM: Artificial Sequence
<220> FEATURE:
<223> OTHER INFORMATION: A synthetic primer

<400> SEQUENCE: 8
tccctacacg acgctcttcc gatctatgtc agggagacaa gaataaacgc tc            52

<210> SEQ ID NO 9
<211> LENGTH: 52
<212> TYPE: DNA
<213> ORGANISM: Artificial Sequence
<220> FEATURE:
<223> OTHER INFORMATION: A synthetic primer

<400> SEQUENCE: 9
tccctacacg acgctcttcc gatctgtccg cgggagacaa gaataaacgc tc            52

<210> SEQ ID NO 10
<211> LENGTH: 52
<212> TYPE: DNA
<213> ORGANISM: Artificial Sequence
<220> FEATURE:
<223> OTHER INFORMATION: A synthetic primer

<400> SEQUENCE: 10
tccctacacg acgctcttcc gatctcttgt agggagacaa gaataaacgc tc            52

```
<210> SEQ ID NO 11
<211> LENGTH: 32
<212> TYPE: DNA
<213> ORGANISM: Artificial Sequence
<220> FEATURE:
<223> OTHER INFORMATION: A synthetic primer

<400> SEQUENCE: 11
gagctcttcc gatctgcctg ttgtgagcct cc                                        32

<210> SEQ ID NO 12
<211> LENGTH: 58
<212> TYPE: DNA
<213> ORGANISM: Artificial Sequence
<220> FEATURE:
<223> OTHER INFORMATION: A synthetic primer

<400> SEQUENCE: 12
aatgatacgg cgaccaccga gatctacact ctttccctac acgacgctct tccgatct            58

<210> SEQ ID NO 13
<211> LENGTH: 34
<212> TYPE: DNA
<213> ORGANISM: Artificial Sequence
<220> FEATURE:
<223> OTHER INFORMATION: A synthetic primer

<400> SEQUENCE: 13
caagcagaag acggcatacg agctcttccg atct                                      34

<210> SEQ ID NO 14
<211> LENGTH: 100
<212> TYPE: DNA
<213> ORGANISM: Artificial Sequence
<220> FEATURE:
<223> OTHER INFORMATION: Aptamer

<400> SEQUENCE: 14
gcctgttgtg agcctcctgt cgaacaacca ctcatatcta ctacatgact tgctccattc          60
tgttctttct ctacgcattg agcgtttatt cttgtctccc                                100

<210> SEQ ID NO 15
<211> LENGTH: 100
<212> TYPE: DNA
<213> ORGANISM: Artificial Sequence
<220> FEATURE:
<223> OTHER INFORMATION: Aptamer

<400> SEQUENCE: 15
gcctgttgtg agcctcctgt cgaacgtatt tcttgcttcc ttccttgccg cgcacattgc          60
agtataagta cctgtcgttg agcgtttatt cttgtctccc                                100

<210> SEQ ID NO 16
<211> LENGTH: 100
<212> TYPE: DNA
<213> ORGANISM: Artificial Sequence
<220> FEATURE:
<223> OTHER INFORMATION: Aptamer

<400> SEQUENCE: 16
gcctgttgtg agcctcctgt cgaaactgta cttcactttt acctcctctt gctcttatct          60
gtactattgt ctctccgttg agcgtttatt cttgtctccc                                100

<210> SEQ ID NO 17
```

```
<211> LENGTH: 100
<212> TYPE: DNA
<213> ORGANISM: Artificial Sequence
<220> FEATURE:
<223> OTHER INFORMATION: Aptamer

<400> SEQUENCE: 17
gcctgttgtg agcctcctgt cgaaccctat cttgttcatg ctattctcaa tattttcggt    60
tcacttaccg tctgcctttg agcgtttatt cttgtctccc                         100
```

SELECTION AND OPTIMIZATION OF APTAMERS TO RECOGNIZE EBOLA MARKERS

GOVERNMENT LICENSE RIGHTS

This invention was made with government support under 1R43AI118139-01 awarded by National Institutes of Health. The government has certain rights in the invention.

BACKGROUND

Ebolavirus outbreaks are devastating, unpredictable and occurring with increasing frequency in Central and West Africa. The West African Ebola virus (EBOV) epidemic occurred from 2014 to 2016, beginning in Guinea and spreading to Liberia and Sierra Leone. This EBOV outbreak was the most widespread, largest and most severe ever with respect to the number of cases and fatalities, with more than 28,000 individuals infected and ~11,000 deaths. It took more than a month for definitive confirmation that this hemorrhagic fever outbreak was due to EBOV, highlighting problems associated with the dismal state of filovirus diagnosis. Most recently, a small 2017 outbreak was documented in the Democratic Republic of the Congo, demonstrating the wide geographic distribution of the unidentified animal reservoir for the virus. Better, faster and simpler diagnostics are needed to allow rapid control of an emerging outbreak. As well as the ever-present danger of outbreaks in endemic areas, ebolaviruses also pose a potential worldwide danger as they could be used as bioterrorism agents or in biological warfare. Four species of pathogenic ebolavirus circulating in Africa, any of which could cause the next natural or man-made outbreak. To control an ebolavirus outbreak, it is essential to rapidly identify and isolate infected individuals.

SUMMARY

In one aspect, the present description relates to an aptamer. The aptamer includes a DNA sequence with at least 80% identity to SEQ ID NO: 14, SEQ ID NO: 15, SEQ ID NO: 16 and/or SEQ ID NO: 17 and binds to a marker of ebola virus. The ebola virus marker may be sGP. The aptamer may have a DNA sequence having at least 90% sequence identity to SEQ ID NO: 14, SEQ ID NO: 15, SEQ ID NO: 16 and/or SEQ ID NO: 17. The aptamer may have a DNA sequence having at least 95% sequence identity to SEQ ID NO: 14, SEQ ID NO: 15, SEQ ID NO: 16 and/or SEQ ID NO: 17. The DNA sequence of the aptamer may be SEQ ID NO: 14, SEQ ID NO: 15, SEQ ID NO: 16 and/or SEQ ID NO: 17. The aptamer may be further modified. The aptamer may include a modified pyrimidine. The aptamer may include a modified purine.

In another aspect, the present description relates to a nucleic acid compound that includes a DNA sequence with at least 80% identity to SEQ ID NO: 14, SEQ ID NO: 15, SEQ ID NO: 16 and/or SEQ ID NO: 17. The nucleic acid compound may have a DNA sequence having at least 90% sequence identity to SEQ ID NO: 14, SEQ ID NO: 15, SEQ ID NO: 16 and/or SEQ ID NO: 17. The nucleic acid compound may have a DNA sequence having at least 95% sequence identity to SEQ ID NO: 14, SEQ ID NO: 15, SEQ ID NO: 16 and/or SEQ ID NO: 17. The nucleic acid compound may include DNA sequence that includes SEQ ID NO: 14, SEQ ID NO: 15, SEQ ID NO: 16 and/or SEQ ID NO: 17. The nucleic acid compound may be further modified. The nucleic acid compound may include a modified pyrimidine. The nucleic acid compound may include a modified purine.

In yet another aspect, the present description relates to a method of detecting the presence of ebola virus in a test sample. The method can include contacting the test sample with an aptamer that binds to a marker of the ebola virus. The marker may be sGP. The aptamer used to bind the marker of the ebola virus may be an oligonucleotide selected from SEQ ID NO: 14, SEQ ID NO: 15, SEQ ID NO: 16 and/or SEQ ID NO: 17. The aptamer used to bind the marker of the ebola virus may be an oligonucleotide with at least 80% identity to SEQ ID NO: 14, SEQ ID NO: 15, SEQ ID NO: 16 and/or SEQ ID NO: 17. The aptamer used to bind the marker of the ebola virus may be an oligonucleotide with at least 90% identity to SEQ ID NO: 14, SEQ ID NO: 15, SEQ ID NO: 16 and/or SEQ ID NO: 17. The aptamer used to bind the marker of the ebola virus may be an oligonucleotide with at least 95% identity to SEQ ID NO: 14, SEQ ID NO: 15, SEQ ID NO: 16 and/or SEQ ID NO: 17. The test sample may be a serum sample, tissue sample, cell sample or a saliva sample. The method may further include processing the test sample to expose the marker to the aptamer. The method may include immobilizing the aptamer on a solid support. The method may further include depositing the sample on a membrane, adding an aptamer to the membrane wherein the aptamer is labeled with a detectable label. The method may further include removing unbound aptamer and detecting bound labeled aptamer to the ebola marker.

In a further aspect, the present description also relates to a kit that includes an aptamer, wherein the aptamer includes a DNA sequence with at least 80% identity to SEQ ID NO: 14, SEQ ID NO: 15, SEQ ID NO: 16 and/or SEQ ID NO: 17 and binds to sGP of ebola virus. The kit may also include a DNA sequence selected from the group consisting of SEQ ID NO: 14, SEQ ID NO: 15, SEQ ID NO: 16 and SEQ ID NO: 17.

BRIEF DESCRIPTION OF THE DRAWINGS

FIG. 2 is a binding isotherm for aptamer 6011 (SEQ ID NO:14) with EBOV sGP in the presence or absence of 1% human serum or with SUDV sGP or with Lcn2 in the absence of serum.

DETAILED DESCRIPTION OF ILLUSTRATIVE EMBODIMENTS

Figure 1A:
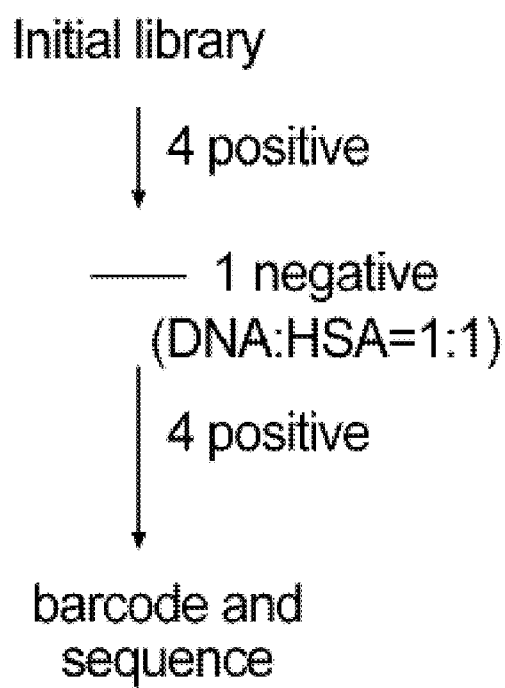
FIG. 1A is a schematic of the selection protocol for identifying aptamers that bind sGP.

The present description includes detection of ebola virus in an individual by use of aptamers. Aptamers can be identified that bind to markers of ebola virus. In one embodiment, the marker for ebola virus may be soluble glycoprotein (sGP). The present description can also include methods for detecting ebola virus with aptamers that specifically and tightly bind to markers of ebola virus in a sample. The present description can include methods of testing an individual for the presence of ebola virus and methods for identifying carriers of ebola virus and controlling an outbreak of an ebola virus disease (EVD) epidemic.

Definitions

Various terms are defined herein. The definitions provided below are inclusive and not limiting, and the terms as used herein have a scope including at least the definitions provided below.

The terms "preferred" and "preferably", "example" and "exemplary" refer to embodiments that may afford certain benefits, under certain circumstances. However, other embodiments may also be preferred or exemplary, under the same or other circumstances. Furthermore, the recitation of one or more preferred or exemplary embodiments does not imply that other embodiments are not useful, and is not intended to exclude other embodiments from the inventive scope of the present disclosure.

The singular forms of the terms "a", "an", and "the" as used herein include plural references unless the context clearly dictates otherwise. For example, the term "a tip" includes a plurality of tips.

Reference to "a" chemical compound refers one or more molecules of the chemical compound, rather than being limited to a single molecule of the chemical compound. Furthermore, the one or more molecules may or may not be identical, so long as they fall under the category of the chemical compound.

The terms "at least one" and "one or more of" an element are used interchangeably, and have the same meaning that includes a single element and a plurality of the elements, and may also be represented by the suffix "(s)" at the end of the element.

The terms "about" and "substantially" are used herein with respect to measurable values and ranges due to expected variations known to those skilled in the art (e.g., limitations and variability in measurements).

The terms "and/or" means one or all of the listed elements or a combination of any two or more of the listed elements.

The terms "comprises," "comprising," and variations thereof are to be construed as open ended—i.e., additional elements or steps are optional and may or may not be present.

As used herein, the term "aptamer" refers to an oligonucleotide that can conform in three-dimensions to bind another molecule with high affinity and specificity.

As used herein, the term "cap" refers to a moiety attached to the 3' or 5' end of an aptamer or other nucleic acid that changes the stability of the nucleic acid, prevent polymerase elongation of the nucleic acid, or may increase the efficiency of nucleic acid dimer formation. The term "capping" refers to the process of adding a cap.

As used herein, "consensus sequence", when used in reference to a series of related nucleic acids, refers to a nucleotide sequence that reflects the most common choice of base at each position in the sequence where the series of related nucleic acids has been subjected to intensive mathematical and/or sequence analysis.

As used herein, the term "detectable label" refers to a molecule or a compound or a group of molecules or a group of compounds associated with a nucleic acid or a polypeptide and is used to identify the nucleic acid or the polypeptide. Signals from the detectable label may be detected by various means and will depend on the nature of the detectable label. Detectable labels may be radioisotopes, fluorescent moieties, colored substances, enzymes, enzyme substrates, and the like. Examples of means to detect detectable label include but are not limited to spectroscopic, photochemical, biochemical, immunochemical, electromagnetic, radiochemical, or chemical means, such as fluorescence, chemifluorescence, or chemiluminescence, or any other appropriate means.

As used herein, the term "amplification" means one or more methods known in the art for copying a target nucleic acid, thereby increasing the number of copies of a selected nucleic acid sequence. Amplification may be exponential or linear. A target nucleic acid may be either DNA or RNA. The sequences amplified in this manner form an "amplicon." While the exemplary methods described hereinafter relate to amplification using the polymerase chain reaction ("PCR"), numerous other methods are known in the art for amplification of nucleic acids (e.g., isothermal methods, rolling circle methods, etc.). The skilled artisan will understand that these other methods may be used either in place of, or together with, PCR methods.

As used herein, the term "sample" means any tissue or body fluid that can be isolated from the body of an individual. A sample may include, for example, a tissue biopsy, blood, plasma, serum, bile, saliva, urine, tears, perspiration, and the like.

As used herein, "ebola" can refer to "ebola virus" and the two terms can be used interchangeably.

In some embodiments, the present description can include aptamers that specifically and tightly bind a marker for ebola virus. The aptamers can be oligonucleotides. The aptamer can be, for example, a DNA molecule, a RNA molecule, a DNA:RNA molecule and the like. In some embodiments, the aptamer is a single stranded nucleic acid molecule that can adopt a structure which combines single stranded and double stranded elements. In one embodiment, the aptamers can be DNA aptamers. A variety of DNA aptamers can be identified that can bind to a marker from ebola as described herein.

The present description will refer to DNA aptamers but it will be understood that this description is not limited to DNA aptamers and that other aptamers may also be identified to detect ebola and are also within the scope of this description.

Aptamers described herein can be oligonucleotides that can form a three-dimensional structure that binds another molecule, e.g. a marker for ebola, with high affinity and specificity. Because of their ability to bind a variety of ligands and the ease and range of options for functionalization of nucleic acids, aptamers have been used in place of antibodies in a variety of therapeutic and diagnostic applications. Nucleic acid aptamers can be used as capture moieties, as well as detection moieties in ELISA-like assays as described, for example, in Vivekananda, et al., Lab Invest. 2006 June; 86(6):610-8) and incorporated herein by reference.

In some embodiments, DNA aptamers are identified that bind a marker for the ebola virus. The aptamers may bind the marker from more than one subtype of ebola virus. In one embodiment, DNA aptamers described herein can bind the EBOV sGP. The DNA aptamers may also bind the sGP of ebola virus from a subtype selected from Ebola (EBOV, formerly Zaire), Sudan (SUDV), Tai Forest (TFV) and Bundibugyo (BUNV), Cote D'Ivoire, and Reston. In one embodiment, aptamers disclosed herein can bind sGP from both EBOV and SUDV, the most genetically diverse of the ebolavirus species. The aptamers may bind to highly conserved motifs in sGP and thus bind to different species of ebola virus or they may bind to specific motifs in sGP characteristic of each species Aptamers that bind to a variety of markers for EVD can be used and all are within the scope of this description. Markers for EVD can include, for example, a secreted soluble glycoprotein (sGP), virion-associated GP (precursor of GP1 and GP2) and another secreted protein (ssGP) as described below. In one embodiment, the marker selected for detecting ebola virus is sGP. The sGP can be from EBOV and/or SUDV. sGP's from other subtypes may also be used.

The present description will refer to aptamers that can bind sGP marker from ebola but it will be understood that this description is not limited to aptamers that bind to sGP and that the aptamers may also be identified that bind other markers and that these aptamers are also within the scope of this description.

The markers can be molecules that are secreted by the ebola virus into, for example, the blood or tissue of an individual if the individual is infected with ebola. The marker may be secreted in infected individuals in amounts that do not require extraction or further concentration or purification. Markers that require further processing, e.g. extraction, in order to bind an aptamer may also be used. In some embodiments, blood may be collected from the individual to be tested for the presence of the ebola virus. The blood may be tested for the presence of a marker for ebola virus. The blood may be further processed, for example, to obtain plasma or serum. In some embodiments, serum from an individual may be tested for the presence of a marker for ebola virus by binding of the aptamer. Markers may also be molecules that are within or attached to the virus and may be extracted from a sample obtained from an individual prior to binding the aptamers.

The sGP marker is a homo-dimer linked by two disulfide bonds through residues 53 and 306, and is known to be the predominant protein generated from RNA produced from the GP gene of all ebolavirus species in vivo. The sGP marker can appear at high levels in the blood stream early during infection and can be a biomarker for ebola virus infection. sGP, which does not require extraction can be a desirable biomarker for the development of a diagnostic tool for ebolavirus infection in which it is an abundant soluble protein that can be detected in the blood early in acute infection. Other biomarkers may also be used as a diagnostic tool for ebola virus infection.

The GP gene can also be the most highly expressed genes of all ebolavirus genes in cultured A549 cells infected by the ebolavirus genome, making sGP the most highly produced of all the ebolavirus proteins. sGP is composed of the first 295 amino acids of GP1 with an additional 71 carboxy-terminal residues that are not found in GP1. sGP, which can be abundant during infection, can be released into the serum. Without being bound by any theory, it is believed that sGP can serve as a decoy for immune responses elicited during the infection as well as to serve in other poorly defined roles. Residues in sGP can be 58% identical across the four African subtypes, EBOV, SUDV, TFV and BUNV, with many of the observed residue changes being conservative. Amino acid conservation can be much higher within the receptor binding domain (amino acid 54-201) with 85% of residues that can be conserved between positions 41 and 190 of the divergent EBOV and Sudan virus species.

In addition to sGP, two other proteins can be produced from the GP gene. The virion-associated GP (precursor of GP1 and GP2) and another secreted protein (ssGP) are produced due to a transcriptional frame-shifting event in a 7 adenosine (7A) stretch during GP transcription, resulting in the production of sGP:GP1,2:ssGP in a ratio of 71:24:5. This frame-shifting event likely provides a selective advantage for the virus in vivo. Whereas, in tissue culture the 7A stretch is rapidly replaced by an 8A mutant that solely expresses the virion-associated glycoprotein, in vivo the 8A mutant sequence is rapidly replaced by the WT EBOV sequence that expresses sGP and requires a frame-shifting event to generate the viral GP1,2. The fact that the production of sGP in addition to GP1,2 is selected for in vivo suggests that the production of sGP gives the virus a selective advantage and is very likely to be present in any viral outbreak. Aptamers may be identified that bind to any of the proteins described above.

Aptamers disclosed herein can have high affinities for sGP. In one embodiment, the aptamers, for example, can recognize sGP in the serum of an infected individual.

Aptamers can recognize sGP when the sGP in the serum is at a concentration of greater than about 2 µM. In some embodiments, aptamers can recognize sGP when the sGP in the serum is at a concentration greater than about 2 nM. In one embodiment, aptamers can recognize sGP when the sGP in the serum is at a concentration between about 2 nM to about 2 µM. Detection of sGP by apatamers at concentrations outside this range are also within the scope of this description.

Aptamers disclosed herein can have a variety of affinities to the ebola marker. In some embodiments, the aptamers can have a dissociation constant ($K_d$) of below 500 nM. In some embodiments, the aptamers may have a $K_d$ of below 300 nM. In one embodiment, the aptamers may have a $K_d$ of below 100 nM. In another embodiment, the aptamers may have a $K_d$ of below 50 nM. Aptamers with a $K_d$ outside of these values are also within the scope of this description.

Nucleic acid aptamers can be created using an in vitro process known as systematic evolution of ligands by exponential enrichment (SELEX) as described, for example, in U.S. Pat. No. 8,409,795 to Schneider and Tuerk C. et al Science. 1990:505-510, incorporated herein by reference. Briefly, the selection process uses a combinatorial oligonucleotide library in which each oligonucleotide has central region of variable nucleic acids flanked by two regions of fixed sequence. The variable region of each candidate in the library can be totally or partially randomized. The oligonucleotide library is exposed to a target, such as a marker, e.g. an ebola virus marker, under conditions that allow favorable binding between oligonucleotide candidates and the target. Following binding, a selective partitioning step is utilized, in which non-binding or poorly binding oligonucleotides are removed from the mixture, and the oligonucleotide candidates that bound to the target are then removed from the target molecule. These selected oligonucleotides are then enriched using PCR amplification with primers to the fixed regions of the oligonucleotide candidates. This process of binding, selective partitioning, and amplifying the selected candidate oligonucleotides is repeated for several rounds. The selected sequences can then be sequenced.

In one embodiment, the SELEX process can be used to identify DNA aptamers as exemplified below in the Examples. Exemplary aptamers are disclosed herein and can include nucleic acid sequences disclosed in SEQ ID NO:14, SEQ ID NO:15, SEQ ID NO:16 and/or SEQ ID NO:17. The sequences listed in SEQ ID NOs:14-17 can bind to the sGP marker of the ebola virus.

In further embodiments, the present disclosure can provide an aptamer(s) that specifically bind to the sGP marker, wherein the primary nucleic acid sequence includes a sequence of contiguous nucleotides that are identical to a sequence of contiguous nucleotides included in any one of SEQ ID NOS: 14-17. For example, in various embodiments, the sequence of contiguous nucleotides in the sGP aptamer can include a sequence of contiguous nucleotides selected from a nucleic acid which is comprised of at least 6 contiguous nucleotides from the sequences of any one of SEQ ID NOs: 14-17; at least 7 contiguous bases from of any one of the SEQ ID NOs: 14-17; of at least 8 contiguous bases from of any one of the SEQ ID NOs: 14-17; of at least 9 contiguous bases from of any one of the SEQ ID NOs: 14-17; of at least 10 contiguous bases from of any one of the SEQ ID NOs: 14-17; of at least 11 contiguous bases from of any one of the SEQ ID NOs: 14-17; of at least 12 contiguous bases from of any one of the SEQ ID NOs: 14-17; of at least 13 contiguous bases from of any one of the SEQ ID NOs: 14-17; of at least 14 contiguous bases from of any one of the SEQ ID NOs: 14-17; and of at least 15 contiguous bases from of any one of the SEQ ID NOs: 14-17.

The aptamers described herein may include motifs. "Motifs" as used herein relate to bases that can be highly conserved at some positions but have variability at other positions without significantly affecting the motif. In one embodiment, the aptamers can have a "TTTTCT" motif. In some embodiments, this motif may vary by one and/or two bases.

The present description can also include a nucleic acid molecule or construct that includes the aptamers disclosed herein. The nucleic acid molecule can contain an aptamer(s) described herein. The nucleic acid molecule may contain any number of nucleotides in addition to the sGP binding region of the aptamer. In various embodiments, the nucleic acid molecule can include up to about 150 nucleotides, up to about 100 nucleotides, up to about 90 nucleotides, up to about 85 nucleotides, up to about 80 nucleotides, up to about 75 nucleotides, up to about 70 nucleotides, up to about 65 nucleotides, up to about 60 nucleotides, up to about 55 nucleotides, up to about 50 nucleotides, up to about 45 nucleotides, up to about 40 nucleotides, up to about 35 nucleotides, up to about 30 nucleotides, up to about 25 nucleotides, and up to about 20 nucleotides in addition to the sGP binding region of the aptamer.

Nucleotides in the aptamers can be modified in any number of ways, including modifications of the ribose and/or phosphate and/or base positions. Certain modifications are described in U.S. Pat. No. 5,660,985 entitled "High Affinity Nucleic Acid Ligands Containing Modified Nucleotides", U.S. Pat. No. 5,428,149 entitled "Method for Palladium Catalyzed Carbon-Carbon Coupling and Products", U.S. Pat. No. 5,580,972 entitled "Purine Nucleoside Modifications by Palladium Catalyzed Methods", U.S. Pat. No. 5,719,273 entitled "Nucleoside modifications by palladium catalyzed methods" all of which are incorporated by reference herein in their entirety. In one embodiment, modifications are those wherein another chemical group is attached to the 5-position of a pyrimidine or the 2' position of a sugar. There is no limitation on the type of other chemical group that can be incorporated on the individual nucleotides. In some embodiments, the resulting modified nucleotide is amplifiable or can be modified subsequent to the amplification steps (see, e.g., U.S. Pat. No. 6,300,074 entitled "Systematic evolution of ligands by exponential enrichment: ChemiSELEX").

Nucleotides in aptamers may be chemically modified, singly or in any combination. The sugars and/or the bases of the nucleotides may be modified. Nucleotide chemical modifications in aptamers may include, for example, 2'-position sugar modifications, 5-position pyrimidine modifications (e.g., 5-(N-benzylcarboxyamide)-2'-deoxyuridine, 5-(N-isobutylcarboxyamide)-2'-deoxyuridine, 5-(N-tryptaminocarboxyamide)-2'-deoxyuridine, 5-(N-[1-(3-trimethylamonium) propyl]carboxyamide)-2'-deoxyuridine chloride, 5-(N-naphthylmethylcarboxamide)-2'-deoxyuridine, or 5-(N-[1-(2,3-dihydroxypropyl)]carboxyamide)-2'-deoxyuridine), modifications at exocyclic amines, backbone modifications, methylations, unusual base-pairing combinations such as the isobases, isocytidine and isoguanidine, and the like.

In some embodiments, the term "C-5 modified pyrimidine" refers to a pyrimidine with a modification at the C-5 position. Examples of a C-5 modified pyrimidine include those described in U.S. Pat. Nos. 5,719,273 and 5,945,527 and incorporated herein by reference. Other modified bases may also be used and are within the scope of this disclosure.

Aptamer modifications may include nucleotide additions or modifications at the 3' and 5' ends, such as a cap or pegylation. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present in a sugar may be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, or organic capping group moieties of from about 1 to about 20 polyethylene glycol (PEG) polymers or other hydrophilic or hydrophobic biological or synthetic polymers. If present, a modification to the nucleotide structure may be imparted before or after assembly of a polymer. A sequence of nucleotides may be interrupted by non-nucleotide components. A polynucleotide may be further modified after polymerization, such as by conjugation with a labeling component.

Inverted nucleotides may be used as cap on the 3' or 5' end of a nucleic acid. As used herein, the term "inverted nucleotide" means deoxyribonucleotides or ribonucleotides having an orientation opposite to that of the sequence that contains them. Classically, with synthesis taking place in the 3' to 5' direction, inverted nucleotides are introduced following or before the rest of the nucleotide strand, in the 5' to 3' direction. The inverted nucleotides and the rest of the strand are then joined together by a 5'-5' or 3'-3' bond. Reference may be made to Koga M., et al., J. Org. Chem., 1991, 56, 3757. The inverted nucleotides can optionally include at least one modified nucleotide, for example at least one nucleotide having a modified nucleic acid base, such as inosine, methyl-5-deoxycytidine, dimethylamino-5-deoxyuridine, deoxyuridine, diamino-2,6-purine, bromo-5-deoxyuridine or any other modified base permitting hybridization.

Polynucleotides can also contain analogous forms of ribose or deoxyribose sugars that are generally known in the art, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages may be replaced by alternative linking groups. These alternative linking groups include embodiments wherein phosphate is replaced by P(O)S ("thioate"), P(S)S ("dithioate"), (O)NR$_2$ ("amidate"), P(O)R', P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

In some embodiments, the present disclosure can provide an aptamer that specifically binds to the sGP marker and includes a primary nucleic acid sequence. In one embodiment, the primary nucleic acid sequence of the aptamer is selected from SEQ ID NO:14, SEQ ID NO:15, SEQ ID NO:16 and/or SEQ ID NO:17. In other embodiments, the primary nucleic acid sequence is selected such that it is at least 75% identical, at least about 80% identical, at least about 85% identical, at least about 90% percent identical, at least about 91% identical, at least about 92% identical, at least about 93% identical, at least about 94% identical, or at least about 95% identical to a primary nucleic acid sequence selected from SEQ ID NO:14, SEQ ID NO:15, SEQ ID NO:16 and/or SEQ ID NO:17.

The terms "sequence identity", "percent sequence identity", "percent identity", "% identical", "% identity", and variations thereof, when used in the context of two nucleic acid sequences, are used interchangeably to refer to the number of nucleotide bases that are the same in a query nucleic acid or a portion of a query nucleic acid, when it is compared and aligned for maximum correspondence to a reference nucleic acid, divided by either (1) the number of nucleotide bases in the query sequence between and including the most 5' corresponding (i.e., aligned) nucleotide base and the most 3' corresponding (i.e., aligned) nucleotide base, or (2) the total length of the reference sequence, whichever is greater. Exemplary alignment of sequences for comparison can be conducted, e.g., by the local homology algorithm of Smith and Waterman, Adv. Appl. Math., 2:482, 1981, by the homology alignment algorithm of Needleman and Wunsch, J. Mol. Biol., 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel, F. M., et al., Current Protocols in Molecular Biology, pub. by Greene Publishing Assoc. and Wiley-Interscience (1987)).

One example of an algorithm that is suitable for determining percent sequence identity is the algorithm used in the basic local alignment search tool (hereinafter "BLAST"), see, e.g. Altschul, et al., J. Mol. Biol. 215:403-410, 1990 and Altschul, et al., Nucleic Acids Res., 15:3389-3402, 1997. Software for performing BLAST analyses is publicly available through the National Center for Biotechnology Information (hereinafter "NCBI"). The default parameters used in determining sequence identity using the software available from NCBI, e.g., BLASTN (for nucleotide sequences) are described in McGinnis, et al., Nucleic Acids Res., 32:W20-W25, 2004.

As used herein, when describing the percent identity of a nucleic acid, such as a sGP aptamer, the sequence of which is at least, for example, about 95% identical to a reference nucleotide sequence, it is intended that the nucleic acid sequence is identical to the reference sequence except that the nucleic acid sequence may include up to five point mutations per each 100 nucleotides of the reference nucleic acid sequence. In other words, to obtain a desired nucleic acid sequence, the sequence of which is at least about 95% identical to a reference nucleic acid sequence, up to 5% of the nucleotides in the reference sequence may be deleted or substituted with another nucleotide, or some number of nucleotides up to 5% of the total number of nucleotides in the reference sequence may be inserted into the reference sequence (referred to herein as an insertion). These mutations of the reference sequence to generate the desired sequence may occur at the 5' or 3' terminal positions of the reference nucleotide sequence or anywhere between those terminal positions, interspersed either individually among nucleotides in the reference sequence or in one or more contiguous groups within the reference sequence. Further, it is intended that a nucleotide base is considered "identical" for the purposes of determining percent identity, when the nucleotide base (1) is the same as the nucleotide base in the reference sequence, or (2) is derived from the nucleotide base in the reference sequence, or (3) is derived from the same nucleotide base from which the nucleotide base in the reference sequence is derived. For example, 5-methyl cytosine is considered to be "identical" to cytosine for the purposes of calculating percent identity. Similarly, the modified uredines can be considered to be identical to one another for the purpose of determining percent identity. The reference sequence may be any one of the entire nucleotide sequences shown in SEQ ID NOS: 14 to 17, or any fragment of any of these sequences.

Aptamers may be labeled with a detectable label using several methods known by those having ordinary skill in the art. Signals from the detectable label may be detected by various means and will depend on the nature of the detectable label. Detectable labels include but are not limited to fluorophores, radioisotopes (e.g., $^{32}$P, $^{33}$P, $^{35}$S, $^{3}$H, $^{14}$C, $^{125}$, $^{131}$I) electron-dense reagents (e.g., gold, silver), nanoparticles, enzymes commonly used in an ELISA (e.g., horseradish peroxidase, beta-galactosidase, luciferase, alkaline phosphatase), chemiluminescent compound, colorimetric labels (e.g., colloidal gold), magnetic labels (e.g., Dynabeads™), biotin, digoxigenin, haptens, proteins for which antisera or monoclonal antibodies are available, ligands, hormones, oligonucleotides capable of forming a complex with the corresponding oligonucleotide complement.

Detectable labels may be incorporated into nucleic acids by covalent or non-covalent means, e.g., by transcription, such as by random-primer labeling using Klenow polymerase, or nick translation, or, amplification, or equivalent as is known in the art. For example, a nucleotide base is conjugated to a detectable moiety, such as a fluorescent dye, e.g., Cy3™ or Cy5™ and then incorporated into nucleic acid probes during nucleic acid synthesis or amplification. Nucleic acid probes may be labeled when synthesized using Cy3™- or Cy5™-dCTP conjugates mixed with unlabeled dCTP.

For example, fluorescently-labeled nucleotides are commercially available and may be enzymatically incorporated into oligonucleotides (e.g. ChromaTide™ nucleotides from Life Technologies/Invitrogen, described in The Molecular Probes Handbook, 11$^{th}$ Edition, section 8.2). In another exemplary method, amine-reactive nucleotides may be incorporated into an oligonucleotide and then amine-reacted with a desired fluorophore (e.g. ARES™ Nucleic Acid Labeling Kits from Life Technologies/Invitrogen, described in The Molecular Probes Handbook, 11$^{th}$ Edition, section 8.2). Another method of labeling oligonucleotides utilizes a platinum-based chemistry system to link molecules with guanine-based nucleotides (e.g. ULYSIS™ Nucleic Acid Labeling Kits from Life Technologies/Invitrogen, described in The Molecular Probes Handbook, 11$^{th}$ Edition, section 8.2).

Nucleic acid probes may be labeled by non-covalent means known in the art. For example, Kreatech Biotechnology's Universal Linkage System® (ULS®) provides a non-enzymatic labeling technology, wherein a platinum group forms a co-ordinative bond with DNA, RNA or nucleotides by binding to the N7 position of guanosine. This technology may also be used to label proteins by binding to nitrogen and sulfur containing side chains of amino acids. See, e.g., U.S. Pat. Nos. 5,580,990; 5,714,327; and 5,985,566; and European Patent No. 0539466.

Labeling with a detectable label also may include nucleic acid probes attached to another biological molecule, such as a nucleic acid, e.g., an oligonucleotide, or a nucleic acid in the form of a stem-loop structure as a "molecular beacon" or an "aptamer beacon". Molecular beacons as detectable moieties are well known in the art; for example, Sokol (Proc. Natl. Acad. Sci. USA (1998), 95:11538-11543) synthesized "molecular beacon" reporter oligodeoxynucleotides with matched fluorescent donor and acceptor chromophores on their 5' and 3' ends. In the absence of a complementary nucleic acid strand, the molecular beacon remains in a stem-loop conformation where fluorescence resonance energy transfer prevents signal emission. On hybridization with a complementary sequence, the stem-loop structure opens increasing the physical distance between the donor and acceptor moieties thereby reducing fluorescence resonance energy transfer and allowing a detectable signal to be emitted when the beacon is excited by light of the appropriate wavelength. See also, e.g., Antony (Biochemistry (2001), 40:9387-9395), describing a molecular beacon consist of a G-rich 18-mer triplex forming oligodeoxyribonucleotide. See also U.S. Pat. Nos. 6,277,581 and 6,235,504.

Nucleic acid aptamers may be amplified by various methods known to the skilled artisan. Nucleic acid amplification may be linear or exponential. Amplification is generally carried out using polymerase chain reaction (PCR) technologies known in the art. See e.g., Mullis and Faloona, Methods Enzymol. (1987), 155:335, U.S. Pat. Nos. 4,683,202, 4,683,195 and 4,800,159.

Oligonucleotide tags may be used to detect and identify aptamers. For example, a known unique sequence of nucleic acids can be added to the 5' or 3' end of an aptamer that can be identified using PCR techniques known in the art. The tag may be recognized by primers used to amplify the aptamer.

Aptamer beacons are similar to molecular beacons; see, e.g., Hamaguchi, Anal. Biochem. (2001), 294:126-131; Poddar, Mol. Cell. Probes (2001), 15:161-167; Kaboev, Nucleic Acids Res. (2000), 28:E94. Aptamer beacons may adopt two or more conformations, one of which allows ligand binding. A fluorescence-quenching pair is used to report changes in conformation induced by ligand binding. See also, e.g., Yamamoto, et al., Genes Cells (2000), 5:389-396; Smirnov, et al., Biochemistry (2000), 39:1462.

Viral sequence evolution in response to selective pressures may occur in ebola viruses as it does with all RNA viruses. This was demonstrated during the West African epidemic. Aptamers, like most antibodies, bind to surface exposed residues on sGP. Thus, it is possible that the sGP epitopes to which the aptamers bind may evolve in the virus with time. However, a notable advantage of using aptamer for sGP detection rather than antibodies is that aptamers with new specificities can readily be selected from aptamer pools in a relatively short period of time using, for example, the methods described herein. In addition, because aptamers are not part of the immune system, there is no selective advantage for a virus to evolve away from an aptamer binding site. This stands in sharp contrast to an antibody epitope. In some embodiments, the aptamers can bind to a different epitope on the sGP than an antibody.

In some embodiments, the aptamers or aptamer constructs described herein may be immobilized on a solid support for detection of an ebola virus marker. A solid support may take any of a variety of configurations ranging from simple to complex. The solid support can have any one of a number of shapes, including a strip, plate, disk, rod, particle, bead, tube, well (microtiter), and the like. The solid support may be porous or non-porous, magnetic, paramagnetic, or non-magnetic, polydisperse or monodisperse, hydrophilic or hydrophobic. The solid support may also be in the form of a gel or slurry of closely-packed (as in a column matrix) or loosely-packed particles.

Aptamer constructs can be attached to a solid support non-covalently using one binding pair member attached to a solid support (covalently or non-covalently) and one binding pair member attached to the aptamer. Binding pairs include biotin and streptavidin, antibody and antigen, the Fab region of an antibody and its antigen, protein A and the Fc domain of IgG, and a single oligonucleotide strand and its complement.

In some embodiments, the binding pair for attaching the aptamer is biotin and streptavidin, wherein the aptamer is biotinylated and the solid support is coated with streptavidin. Methods for biotinylating nucleic acid are known in the art (e.g. by photo-cross linking using EZ-link psoralen-PEO biotin from Pierce Chemical Co., by chemical coupling using Label IT® µArray® Biotin Labeling Kit from Minis Bio Corp., PFP Biotin from Pierce Chemical Co., by nick translation using BioNick DNA Labeling System from Invitrogen corporation, or by 3'-end labeling using commercially available kits e.g. Biotin 3-end labeling kit from Pierce).

Aptamers can also be covalently attached to a solid support using functionalization chemistry for creating microarrays or nucleotide-coated beads. If covalent bonding between the genomic nucleic acid and the surface is desired, the solid surface will usually be functional or be capable of being functionalized. Examples of functional groups used for linking include but are not limited to carboxylic acids, aldehydes, amino groups, cyano groups, ethylenic groups, hydroxyl groups, thiol groups.

The sample to be tested can be applied to the support with the immobilized aptamers. In one embodiment, a labeled aptamer can be immobilized on a solid support, for example, a strip or particle. In one embodiment, sensor platforms can be used that rely on ionic current flow through nanoporous anodized alumina oxide (NAAO) films modified with aptamers. These devices can be small and have several benefits over the currently available methods for ebolavirus detection. The analysis can be done on-site with a much faster turn-around than RT-PCR-based diagnoses. The devices can be stored in the absence of refrigeration, which cannot be done with antibody based assays. In some embodiments, output may be electronic and may be sent to a smartphone using a Bluetooth or wireless connection. This can overcome the difficulty posed by the antibody-based lateral flow immunochromatographic assay now approved by the WHO and FDA for use in detecting ebolavirus in the field. These lateral flow tests have been reported to be difficult to use in the field because personal protective equipment (PPE) is required for clinicians. The NAAO aptasensor can signal the result of the analysis through an earphone enclosed within the PPE and will thereby enable a single clinician or a local caregiver to determine the outcome of each test. This will reduce errors due to the difficult field environment, and will relieve trained personnel to attend to other patients. The electronic signal may also be automatically sent to other receiving stations such as nearby hospitals and clinics to alert personnel to the on-site findings to give them time to prepare for new patients, and can simultaneously be sent to a centralized data collection site that is monitoring the outbreak.

In some embodiments, capture of sGP by affinity extraction can be used to identify sGP in serum or whole blood. An aptamer based sandwich assay (ABSA) can be used and this assay is based on the use of magnetic particles to capture the protein-aptamer complex. This assay takes advantage of the fact that sGP is glycosylated and can bind to concanavalin A (conA). A radiolabeled aptamer that can bind to the immobilized sGP can be isolated from the unbound aptamer and quantified by scintillation chromatography. The ABSA assay with conA can be used to capture sGP with high sensitivity (decrease limit of detection) of the sGP sensors. In some embodiments, filter capture assays and electrochemical assays may also be used.

The present description also includes assays that use aptamers to detect an ebola marker. In some embodiments, the aptamers are the aptamers disclosed in SEQ ID NOs: 14-17 or any modified aptamers of SEQ ID NOs: 14-17 as described herein. In one embodiment, the marker detected by the aptamers is sGP. In some embodiments, the aptamers are labeled with a detectable label as described herein.

Assays that use an aptamer or aptamers to indirectly detect its cognate ligand are described, for example, in U.S. Pat. No. 7,855,054. In these types of assays, an aptamer construct is used to capture a ligand on a solid support, and contacts a sample that may contain the ligand of the aptamer. The aptamer-ligand complex is partitioned from aptamers that are not bound to the ligand, and the aptamer portion of the aptamer-ligand complex is then separated from the ligand. The amount of ligand in the sample is then measured indirectly by detecting and quantifying the amount of aptamer that was bound to the sample ligand. Alternatively, the ligand captured from the sample is measured directly using an antibody or another aptamer that binds to the ligand.

In one embodiment of an assay, a test sample can be placed in a test region of solid surface, e.g. a filter or membrane. An aptamer labeled with a detectable label can be placed on the test region under conditions that the aptamer would bind to an ebola marker if present. The solid surface may be washed, for example, with a buffer to remove any unbound aptamer. The test region can then be analyzed for the presence of labeled aptamer bound to a marker of ebola in the test sample.

In one embodiment, dot blots may be used with, for example, test sample of various concentrations or amounts are placed so that each filter has multiple test samples with increasing or decreasing amounts of the test sample. An aptamer with a detectable label can be placed on all of the regions with test samples and analyzed to identify test regions that bind the aptamer.

The small size and non-protein nature of the aptamers can allow them to be immobilized in dense and well-oriented manner and can be compatible as the recognition element, with many sensor platforms. The sensor platforms can include, for example, quartz crystal microbalances (QCM), surface plasmon resonance (SPR) technology, diamond field effect transistor (FET) technology, electrochemical impedance spectroscopy [EIS], colorimetric and fluorescence-based optical detection. Other sensor platforms may also be used and are within the scope of this description.

In some embodiments, an EIS platform may be used. EIS can provide the advantages of real time monitoring and label free detection, and can be compatible with flexible electronics, disposable sensors and wearable devices. Inkjet printing can also be applied to producing aptamer-based EIS biosensors for their automated mass production with uniform aptamer deposition.

In some embodiments, to detect low concentrations of sGP in the blood, these aptamers can play a different role of concentrating the target prior to their quantification. For this purpose, magnetic beads coated with sGP aptamers can capture sGP from the blood in which they are present at very low concentrations.

In some embodiments, the reported sGP aptamers can be used in fluorescent aptasensors taking advantage of the flexibility of aptamers, which can result in their frequently adopting alternate conformations in the presence or absence of sGP. For these sensors, aptamers are modified in key positions with fluorescent dyes that interact in fluorescence resonance energy transfer (FRET). Upon aptamer binding to sGP, the associated structural change alters the distance between the fluorescent dyes and thus the efficiency of energy transfer. The signal change, manifested as an increase (signal-on mode) or decrease (signal-off mode) in fluorescence, is proportional to the extent of sGP binding. A representative "signal-on" fluorescent aptamer holds a fluorophore, usually at one end, which is quenched by a molecule that is attached to a proximate location in the unoccupied aptamer. Target binding separates fluorophore from quencher allowing recovery of the fluorescent signal which can provide a quantitative measure of the target concentration. FRET can also be used in "signal-off" sensor designs in which the conformational change of the aptamer on target binding brings the donor and quencher into closer proximity with a resulting fluorescence quenching.

In alternative embodiments, signaling an aptamer binding event using fluorescence can be with an oligonucleotide (attenuator) that is complementary to a portion of the aptamer and remains bound to the aptamer in the absence of sGP molecule. The length of the attenuator and its placement on the aptamer can create a condition that prevents aptamer folding to the actively binding conformation, but the affinity of the aptamer for the attenuator should be less than for the sGP molecule. With these requirements fulfilled, the presence of sGP can successfully compete with the attenuator to bind the aptamer and release the attenuator. Such a design can be used for "signal-on" reporting if the target and aptamer are labeled with fluorescent dyes that are optimally placed to interact in FRET while the aptamer and attenuator are hybridized. This format can also be used for a "signal-off" system in which a single fluorophore is attached to the attenuator.

In some embodiments, the sGP aptamers can also be applied to create a paper-based MoS2 nanosheet-mediated FRET aptasensor for rapid sGP diagnosis. This format can use paper test strips impregnated with fluorescently-labeled aptamers and MoS2 nanosheets. The MoS2 can quench the fluorescence until the aptamers are released when they bind their target. These aptasensors can be facile, inexpensive and therefore attractive for point-of-care diagnosis, especially in low-resource areas. Additionally, these sGP aptamers can also be used in electrochemical aptasensors where the structural change in sGP aptamers upon sGP binding can be employed for altering electron-transfer when the aptamers are labeled with a redox-active moiety and immobilized on a conducting support.

The present description can also include methods for detecting ebola virus in an individual. The aptamers disclosed herein can be used in a variety of methods for detecting the markers of ebola virus. The methods can be amenable to any of the assays or sensor systems described herein. Methods that can be used are described, for example, in U.S. Pat. No. 9,651,556, incorporated by herein by reference. In one embodiment, a sample from an individual to be tested for ebola virus can be obtained. A variety of samples, e.g. tissue, serum, saliva and the like as disclosed herein may be obtained. In one embodiment, serum from an individual to be tested can be obtained.

The method can include contacting the test sample with an aptamer under conditions that enable the aptamer to bind to the ebola marker in the test sample, if present. The aptamer may be labeled with a detectable label as described herein. The method may include removing or separating the unbound aptamer from the aptamer that is bound to the ebola marker. Methods are contemplated where the unbound aptamer may not be removed from the bound aptamer, In one embodiment, the method can include isolating, separating or identifying the presence of the aptamer/marker complex in the assay. Other methods of identifying an ebola marker with a specific aptamer are known and are included in the scope of this description.

The present description can also include kits for the detection of ebola virus in a sample from an individual. The kits can include one or more of the aptamers described herein. The aptamers may be labeled appropriately for detection with a detection label. The kit may also include materials to carry out detection of an ebola marker such as strips, or solid supports, buffers, detecting solutions and the like. In one embodiment, a sample, such as a serum sample may be placed in a detecting region of a test strip. A labeled aptamer may be added to the test strip in concentrations sufficient to bind a marker, e.g. sGP, in the test sample. The test region may be washed to remove unbound aptamer. Detecting solutions may be added to identify aptamer that may be bound to sGP markers in the test sample. If the test sample does not have sGP, then there would not be bound aptamer.

Example

Materials and Methods:

SELEX Library Construction

A DNA single stranded oligonucleotide library, named 487D, was synthesized by IDT (Integrated DNA Technologies, Coralville, Iowa) with the following sequence (SEQ ID NO:1): 5'GCCTGTTGTGAGCCTCCTGTCGAA (53N) TTGAGCGTTTATTCTTGTCTCCC 3'. N symbolizes an equimolar mixture of A, C, G and T. The following primers were used for PCR reactions: Oligo 6008 (SEQ ID NO:2) (5' end biotinylated): GGG AGA CAA GAA TAA ACG CTC-3' (IDT Ref No. 135814559) and Oligo 485 (SEQ ID NO:3): 5'-GCCTGTTGTGAGCCTCCTGTCGAA-3 to amplify the pool after each round of selection.

In-Vitro Selection of DNA Aptamers Against sGP (Soluble Glycoprotein)

Systematic Evolution of Ligands by Exponential Enrichment (SELEX) method was carried out for developing the DNA aptamers against sGP. The first round of SELEX was initiated incubating 1λ$10^{15}$ molecules (1.66 nmoles) of ssDNA pool 487D with 0.7 nmoles of sGP. The ionic conditions were maintained using phosphate buffers containing 137 mM NaCl, 2.7 mM KCl, 10 mM $Na_2HPO_4$, 2 mM $KH_2PO_4$ at pH 7 and maintaining magnesium concentration at 5 mM. The non-binding aptamers were removed passing through a nitrocellulose membrane (Milipore Cat #HAWP02500 purchased from MilliporeSigma, Burlington, Mass.) on which the protein and bound DNAs were captured. The protein bound ssDNAs were extracted from the membrane by heating at 80° C. for 10 minutes using freshly prepared 7M Urea and purified through ethanol precipitation. The extracted ssDNAs were amplified through polymerase chain reaction (PCR) using 0.05 U/ul Taq DNA polymerase (GenScript #E00007), Taq Buffer (GenScript #B0005 from GenScript, Piscataway, N.J.) 0.2 mM dNTPs (Genscript #C01582-1), 2 uM each of primer 485 (SEQ ID NO: 3) and Oligo 6008 (SEQ ID NO:2), for the successive rounds. Each time the quality of the PCR product was checked upon running them on 2% agarose gel using TAE buffer (40 mM Tris Acetate, 1 mM EDTA, pH 8) at a constant voltage of 110V. The PCR products were purified using QIAquick PCR Purification Kit (Cat No./ID: 28104) from Qiagen, Valencia, Calif. and quantified using a Nanodrop spectrophotometer ND1000 Spectrophotometer (Nanodrop Technologies) NanoDrop Technologies, Inc., Wilmington, Del. The biotinylated strand was removed using Dynabeads M280 (Dynal Biotech, product no. #650.01) purchased from ThermoFisher Scientific, Waltham, Mass. The ssDNAs were further purified through ethanol precipitation and used for the following rounds of SELEX. Total 8 rounds of SELEX were carried out, with gradual increase of selection pressure by taking ssDNA: sGP ratio (2:1, 3:1, 4:1, 5:1, 6:1, 7:1, 8:1, 10:1). In between $4^{th}$ and $5^{th}$ rounds of SELEX a negative selection has been executed to remove the potential binders of human serum albumin (HSA) from the ssDNA pool.

Next Gen Sequencing Sample Preparation

Samples for next gen sequencing were prepared taking the starting DNA pool along with the DNA samples from rounds 1, 2, 4, 5, 7 and 8. DNAs from different pools were barcoded with different Illumina approved indices. The sequencing was carried out in Illumina HiSeq3000 machine purchased from Illumina, San Diego, Calif. The indices and adaptors were added to the DNA samples through primers during subsequent PCRs. The following primers were used to add the indices (marked in bold letters and underlined) to different DNA samples,

```
Oligo6001 (SEQ ID NO: 4):
5'TCCCTACACGACGCTCTTCCGATCTATCACGGGGAGACAAGAATAAAC
GCTC 3'

Oligo 6002 (SEQ ID NO: 5):
5'TCCCTACACGACGCTCTTCCGATCTTAGCTTGGGAGACAAGAATAAAC
GCTC 3'

Oligo 6003 (SEQ ID NO: 6):
5'TCCCTACACGACGCTCTTCCGATCTGGCTACGGGAGACAAGAATAAAC
GCTC 3'

Oligo 6004 (SEQ ID NO: 7):
5'TCCCTACACGACGCTCTTCCGATCTAGTCAAGGGAGACAAGAATAAAC
GCTC 3'

Oligo 6005 (SEQ ID NO: 8):
5'TCCCTACACGACGCTCTTCCGATCTATGTCAGGGAGACAAGAATAAAC
GCTC 3'
```

Oligo 6006 (SEQ ID NO: 9):
5'TCCCTACACGACGCTCTTCCGATCTGTCCGCGGGAGACAAGAATAAAC
GCTC 3'

Oligo 6007 (SEQ ID NO: 10):
5'TCCCTACACGACGCTCTTCCGATCTCTTGTAGGGAGACAAGAATAAAC
GCTC 3'

The other primer for PCR being same for all the samples as Oligo 3657 (SEQ ID NO:11): 5' GAGCTCTTCC-GATCTGCCTGTTGTGAGCCTCC 3', only one of the strands of the DNA was barcoded.

The primers for adding the adaptors were Oligo 4770 (SEQ ID NO:12):

5'AATGATACGGCGACCACCGAGATCTA-CACTCTTTCCCTACACGACGC TCTTCCGATCT3',

Oligo 4771(SEQ ID NO:13):

5'-CAAGCAGAAGACGGCATACGAGCTCTTCC-GATCT3.

End Labelling the ssDNA Oligos for Characterizing the Potential Aptamers

DNA aptamers were end labelled with $^{32}$P upon incubation with γ$^{32}$P-ATP through an enzymatic reaction involving 0.4 U/ul T4 polynucleotide Kinase (NEB #M0201L) purchased from New England Biolabs, Ipswich, Mass. under a buffer condition of 70 mM Tris HCl, 10 mM MgCl2, 5 mM dithiothreitol, pH 7.6. The labelled oligos were purified using Biospin 6 resins (Bio-Gel P-6 Gel #1504130) purchased from Bio-Rad Laboratories, Hercules, Calif. The percentage of $^{32}$P in the oligos were estimated each time after labelling through ascending thin layer chromatography (ATLC) using P30 Filtermat, WALLAC, cat #1450-523, purchased from PerkinElmer, Waltham, Mass. glass fiber filter with negatively charged P30 active groups, printed, size 90×120 mm, Lot #498518/481108 and a mobile phase of 30% v/v methanol, 10% w/v TCA, 10% v/v acetic acid. The labelled oligos were refolded under the proper ionic conditions as maintained during their development through SELEX, by heating the oligos at 95° C. for 5 minutes followed by incubation at room temperature (23° C.) for 30 minutes before they were screened for their binding efficiency towards the target protein sGP.

Single Well and Dot Blot Filter Capture Assays

The DNA aptamers were incubated with different proteins (sGP, HSA, Uterocalin) under different concentrations (0 nM to 6 uM) to look for their affinity as well as specificity towards sGP. The bound aptamers were screened by passing the aptamer-protein solutions, through nitrocellulose membrane (Milipore Cat #HAWP02500 purchased from MilliporeSigma, Burlington, Mass. for single well binding apparatus and BIO-RAD, 0.45 micron, 30 cm×3.5 m, #162-0115 for dot blot capture assay purchased from Bio-Rad Laboratories, Hercules, Calif. under constant vacuum. The membranes were washed each time with the same buffer in which the aptamer protein binding carried out, both before and after passing the solutions. The bound aptamers were quantified from the membrane, either by using a liquid scintillation counter (Tricarb 4910$^{TR}$, Perkin Elmer (manufactured by PerkinElmer, Waltham, Mass.) or by exposing the membranes to phosphor screen and taking the screen for imaging in a Typhoon Imaging system (GE Healthcare, FLA9500) purchased from GE Healthcare, Chicago, Ill. The data was fit to F=Fmin+(Fmax*L^n)/(L^n+Kd^n) to determine the Kd.

Results

A combination of SELEX, next-generation sequencing and bioinformatics were used to identify DNA aptamers that recognize EBOV sGP specifically and with low nanomolar affinity.

Figure 1B:
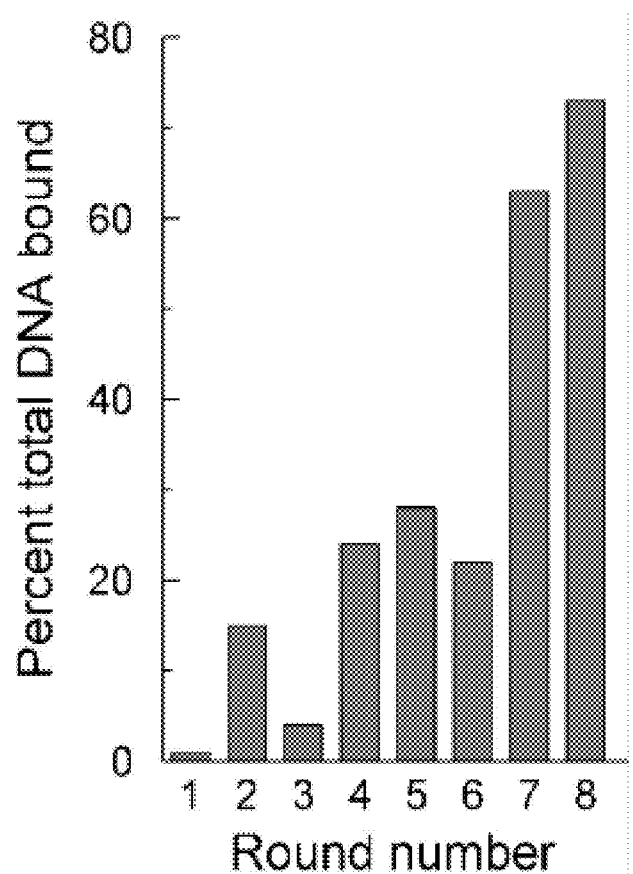
FIG. 1B is a graph of the percent of each successive pool that was captured with EBOV sGP. The percent of DNA captured increased with subsequent rounds of SELEX.

SELEX was used to select DNA oligonucleotides with sequences that endowed them with high affinities for sGP. Single stranded DNA aptamers were obtained by multiple rounds of positive selection against sGP and negative selection against the filter capture matrix and against human serum albumin. The process involved 8 rounds of selection against EBOV sGP or the filter matrix on which the sGP-DNA complex was captured (FIG. 1A). Each subsequent pool was tested for the percent of DNA bound to sGP. An increasing fraction of bound DNA with progressive rounds, as found for this SELEX experiment, is consistent with the selection of aptamers that recognize sGP (See FIG. 1B)

A sample of starting ssDNA library and DNA pools from a series of selection rounds (1, 2, 4, 5, 7, 8) were bar-coded and subjected to high throughput sequencing. The derived sequences (~1.8×10$^6$ per round) were analyzed for a variety of properties. For example, the sequences were clustered by relatedness and separated into families. The families were examined for their appearance and rate of expansion through the course of the SELEX rounds. The sequences were analyzed through the rounds to evaluate the changes expected if selection were occurring, such as a decrease in unique sequences and an increase in an enrichment of certain sequences in subsequent rounds. Comparisons between sequences within the clusters and between clusters were made to search for conserved motifs that might identify the critical components of aptamers. From these studies, we obtained 17,629,720 sequence reads from the 8$^{th}$ round selected pool. These were clustered by sequence identity into 977,613 sequence groups (families). Oligonucleotides representing the most abundant sequence in each of the 10 most populous aptamer families were synthesized and tested for affinity to sGP. Of these oligonucleotides, 5 bound sGP with high affinities, displaying K$_d$ in the range of 20-100 nM as shown in Table 1 below.

TABLE 1

| Oligo (100 nt) | Kd for sGP | Binds GP1,2 | Binding to HSA (up to 6 μM) |
|---|---|---|---|
| 6011 | 30 nM | Yes | No |
| 6012 | 90 nM | Yes (22 nM Kd) | No |
| 6020 | ~30 | Yes | |
| 6021 | 20 nM | | No |
| 6022 | 100 nM | | ~100 μM |

Table 1 shows the estimated affinities of candidate aptamers for EBOV sGP and binding to GP1,2 and HSA. HSA was tested at concentrations up to 6 μM.

The nucleotide sequences of Aptamer 6011, 6012, 6021-6022 are shown below.

Aptamer 6011 (SEQ ID NO: 14):
5'-GCCTG TTGTG AGCCT CCTGT CGAAC
AACCA CTCAT ATCTA CTACA TGACT TGCTC CATTC TGTTC
TTTCT CTACGCATTGAGCGTTTATTCTTGTCTCCC-3'

Aptamer 6012 (SEQ ID NO: 15):
5'-GCCTG TTGTG AGCCT CCTGT CGAAC
GTATT TCTTG CTTCC TTCCT TGCCG CGCAC ATTGC AGTAT
AAGTA CCTGTCGTTGAGCGTTTATTCTTGTCTCCC-3'

```
Aptamer 6021 (SEQ ID NO: 16):
5'-GCCTGT TGTGA GCCTC CTGTC GAAAC
TGTAC TTCAC TTTTA CCTCC TCTTG CTCTT ATCTG TACTA
TTGTC TCTCC GTTGA GCGTT TATTC TTGTC TCCC-3'

Aptamer 6022 (SEQ ID NO: 17):
5'-GCCTG TTGTG AGCCT CCTGT CGAAC
CCTAT CTTGT TCATG CTATT CTCAA TATTT TCGGT TCACT
TACCG TCTGC CTTTG AGCGT TTATT CTTGT CTCCC-3'
```

Figure 2:
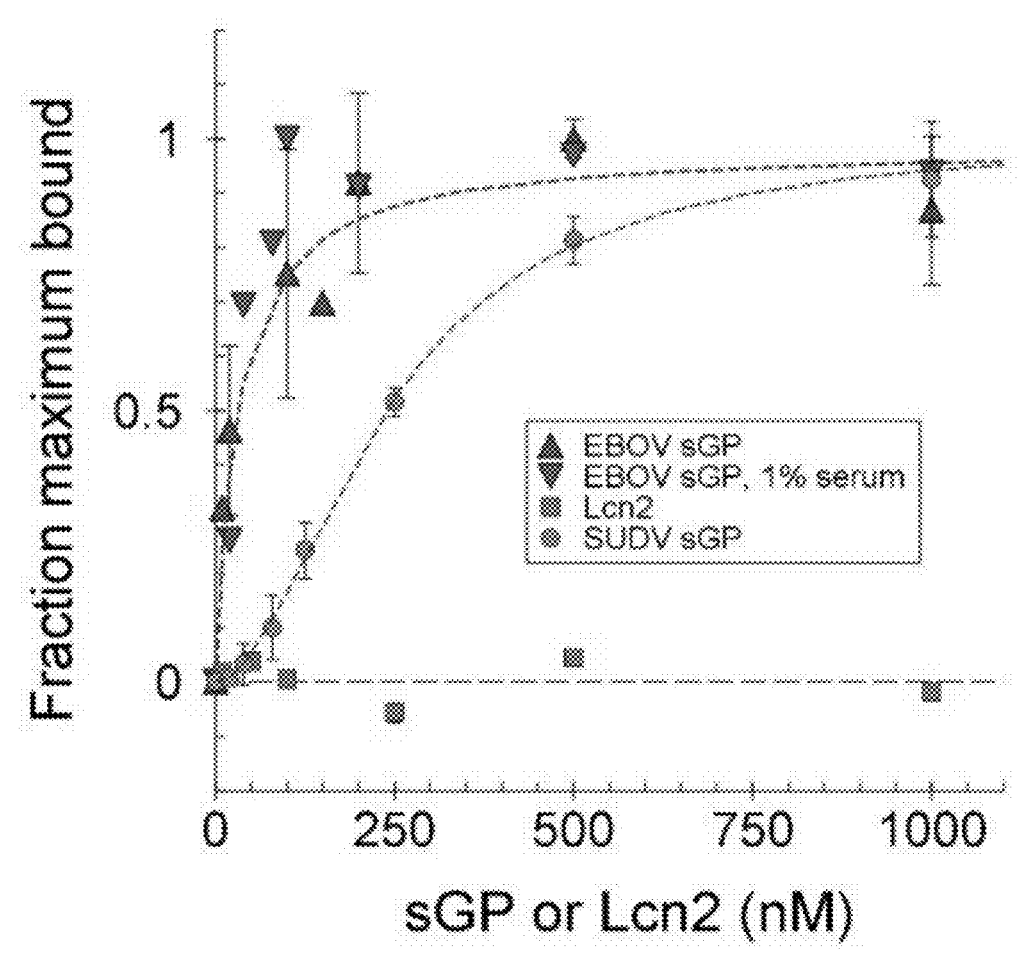

As an example, aptamer 6011 (SEQ ID NO:14) was determined to have a $K_d$ of 30 nM for EBOV sGP in the absence of serum and this was not decreased by the presence of 1% human serum (FIG. 2). Aptamers 6011(SEQ ID NO:14) and 6012 (SEQ ID NO:15) also bound to SUDV sGP, but with slightly lower affinities. One test for specificity for sGP was to test for binding to the protein Lcn2, which is an acute phase protein present in blood at similar concentrations to sGP during EBOV infection. We used recombinant Lcn2, which possesses a His-tag like our recombinant sGP. The Lcn2 was not bound by the aptamers, thus showing specificity for sGP and ruling out the His-tag as the aptamer target (FIG. 2). The estimated $K_d$ for EBOV sGP (dashed fit line) was 30 nM and for SUDV sGP was 240 nM as shown in FIG. 2. Aptamer 6011 (SEQ ID NO:14) did not bind Lcn2, which also contains a His-tag.

Figure 3:
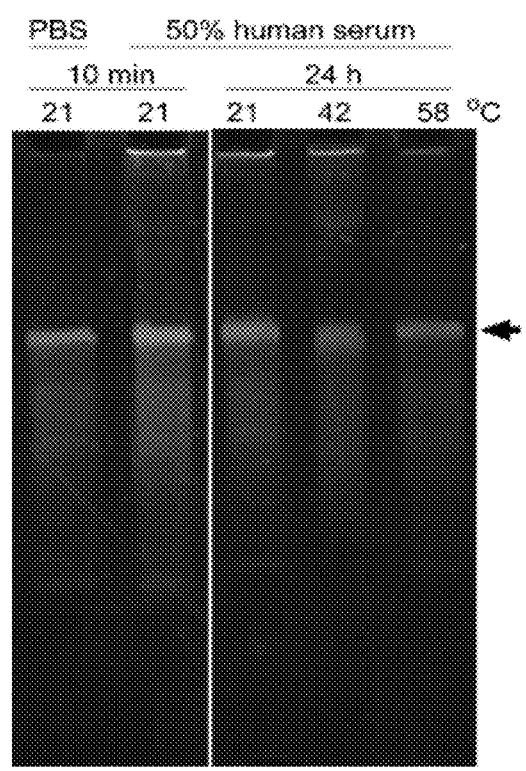
FIG. 3 is a picture of urea polyacrylamide gel of aptamer 6011 (SEQ ID NO:14) incubated at different temperatures with PBS alone or 50% human serum in PBS.

From these studies, aptamers 6011 and 6012 were identified as suitable candidates. Aptamers 6011(SEQ ID NO:14) and 6012 (SEQ ID NO:15) were tested for structural stability in serum. As shown in FIG. 3, the results show that they are stable for 24 h in 50% human serum (shown for oligo 6011 (SEQ ID NO:14) In FIG. 3, samples were incubated for 10 min or 24 h in 50% human serum in PBS or in PBS alone at 21, 42 or 58° C. The treated samples were resolved through a urea polyacrylamide gel. The arrow identifies the location of the aptamer. The upper bright band marks the bottom of the wells where some serum protein accumulated.

The aptamers remain largely intact. The aptamers may be modified for functional stability.

Although the present invention has been described with reference to preferred embodiments, workers skilled in the art will recognize that changes may be made in form and detail without departing from the spirit and scope of the invention.

What is claimed is:

1. An aptamer comprising a DNA sequence, wherein the DNA sequence is SEQ ID NO: 14, SEQ ID NO: 15, SEQ ID NO: 16 and/or SEQ ID NO: 17, wherein the aptamer is capable of binding to a marker of ebola virus and wherein the marker is a protein produced from the glycoprotein (GP) gene.

2. The aptamer of claim 1, wherein the marker is sGP.

3. The aptamer of claim 1, wherein the aptamer is further modified.

4. The aptamer of claim 1, wherein the aptamer comprises a modified pyrimidine.

5. The aptamer of claim 1, wherein the aptamer comprises a modified purine.

6. A nucleic acid compound comprising a DNA sequence with at least 80% identity to SEQ ID NO: 14, SEQ ID NO: 15, SEQ ID NO: 16 and/or SEQ ID NO: 17.

7. The nucleic acid compound of claim 6, wherein the DNA sequence has at least 95% sequence identity to SEQ ID NO: 14, SEQ ID NO: 15, SEQ ID NO: 16 and/or SEQ ID NO: 17.

8. The nucleic acid compound of claim 6, wherein the DNA sequence is SEQ ID NO: 14, SEQ ID NO: 15, SEQ ID NO: 16 and/or SEQ ID NO: 17.

9. A method of detecting the presence of ebola virus in a test sample comprising contacting the test sample with an aptamer of claim 1 that binds to a marker of the ebola virus, wherein the marker is a protein produced from the glycoprotein (GP) gene.

10. The method of claim 9, wherein the marker is sGP.

11. The method of claim 9, wherein the test sample is a serum sample, tissue sample, cell sample or a saliva sample.

12. The method of claim 9, further comprising processing the test sample to expose the marker to the aptamer.

13. The method of claim 9, further comprising immobilizing the aptamer on a solid support.

14. The method of claim 9, further comprising depositing the aptamer on a membrane, wherein the aptamer is labeled with a detectable label and adding the labeled aptamer to the sample on the membrane.

15. The method of claim 14, further comprising removing the aptamer that is not bound to the ebola marker and detecting the labeled aptamer bound to the ebola marker.

16. A kit comprising an aptamer, wherein the aptamer comprises a DNA sequence, wherein the DNA sequence is SEQ ID NO: 14, SEQ ID NO: 15, SEQ ID NO: 16 and/or SEQ ID NO: 17 and wherein the aptamer binds to sGP of ebola virus.

* * * * *